United States Patent [19]

Peterson

[11] 4,441,220

[45] Apr. 10, 1984

[54] RECREATIONAL APPARATUS

[76] Inventor: Lester W. Peterson, Lafayette, Minn. 56054

[21] Appl. No.: 339,484

[22] Filed: Jan. 15, 1982

[51] Int. Cl.³ ............................................... A47G 9/00
[52] U.S. Cl. ............................................. 5/431; 5/61; 128/376
[58] Field of Search ................................. 5/1, 60–62, 5/433, 431; 128/377, 376; 297/313, 330; 108/1

[56] References Cited

U.S. PATENT DOCUMENTS

| 62,010 | 2/1867 | Cagshall | 5/1 |
| 3,835,482 | 9/1974 | Tersch | 128/372 |
| 3,908,666 | 9/1975 | Osborne | 128/372 |
| 4,140,128 | 2/1979 | Van Der Schaaf | 108/20 |
| 4,379,588 | 4/1983 | Speice | 297/330 |

Primary Examiner—Alexander Grosz
Assistant Examiner—Michael F. Trettel
Attorney, Agent, or Firm—Williamson, Bains, Moore & Hansen

[57] ABSTRACT

An outdoor article of furniture includes a base and an elongate bed-like support mounted on the base for rotation and limited tilting movement relative to the base. Power means are provided and rotate the support at a rate of two revolutions per hour so that a user lying on the support will obtain an even sun tan on that portion of the user's body exposed to the sun. When the support is in a tilted position, there will be a tendency to cause a user reclining thereon to roll over when the support is moved through a half rotation, which occurs after a 15-minute interval. Thus, the apparatus itself could urge the user to turn over periodically and thereby minimize the occurence of sunburns caused by overexposure of a portion of the user's body to the sun.

6 Claims, 6 Drawing Figures

U.S. Patent    Apr. 10, 1984    4,441,220
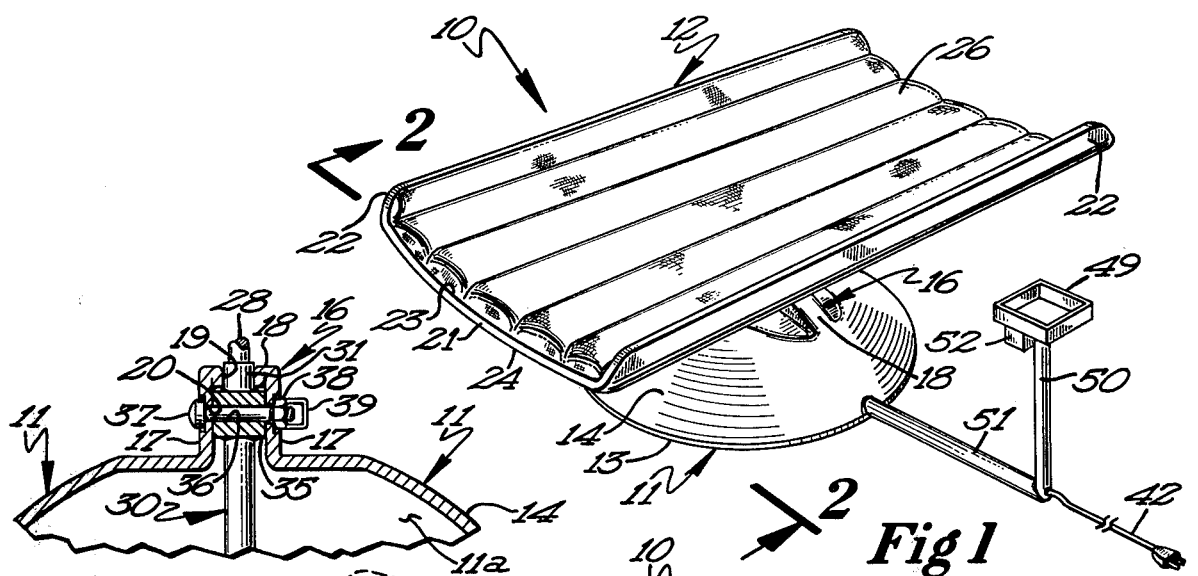
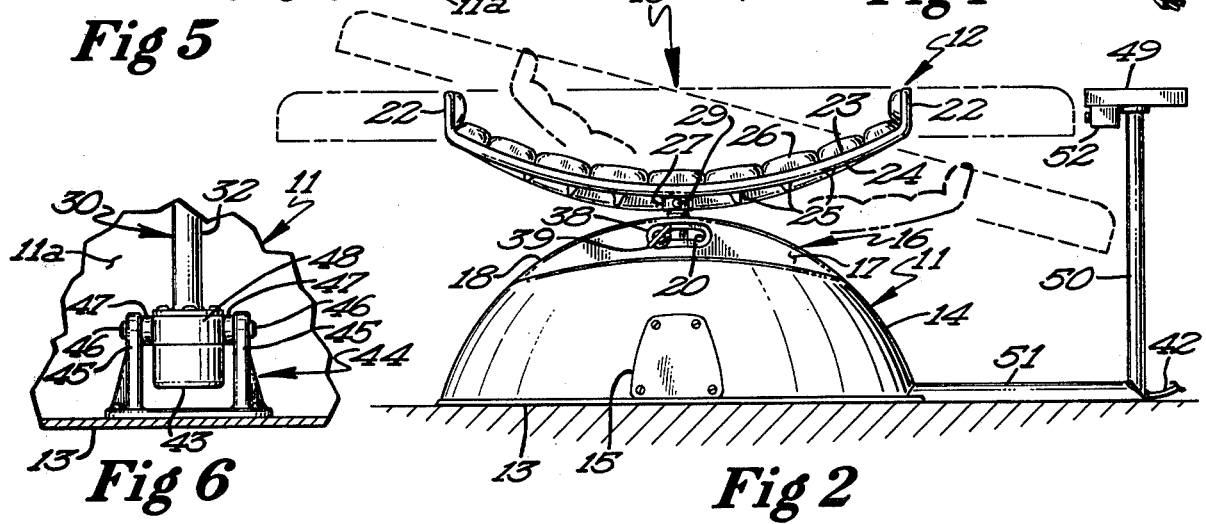
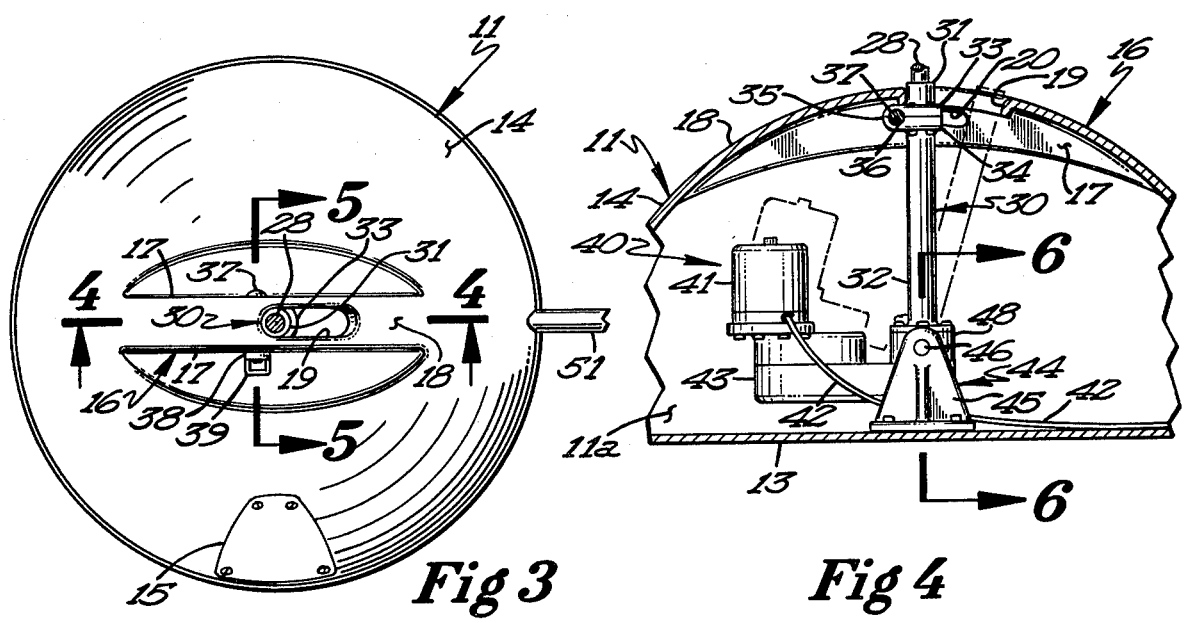

RECREATIONAL APPARATUS

BACKGROUND OF THE INVENTION

This invention relates to an outdoor article of furniture which is operable to permit a user reclining thereon to obtain an even suntan while minimizing the occurance of sunburn due to overexposure to the sun.

Sunbathers desiring to obtain a suntan typically lie upon the beach or poolside, either directly upon the ground or in beach-type furniture.

One of the more obvious problems associated with sunbathing is overexposure which may result in severe burns. In this regard, sunbathers alternately lie on their back or their stomach in order to obtain an even tan and in order to avoid overexposure. Sunbathers also attempt to properly align themselves with respect to the sun to maximize the exposure of certain parts of their body for some predetermined period of time. Since the optimum angle for exposure to the sun constantly changes, a sunbather must also constantly adjust his position with respect to the sun. None of the conventional beach-type furniture used by sunbathers has the capability of self-adjustment to properly position the user for optimum exposure to the sun so that the user may obtain an even tan.

It is therefore the general object of this invention to provide an outdoor article of furniture which supports the user in a reclining position and which is continuously adjustable for positioning the user at the optimum angle with respect to the sun to permit the user to obtain an even tan with respect to the surface exposed.

Another object of this invention is to provide an article of outdoor furniture of the type described which is revolvable about a generally vertical axis to generally follow the sun and which is capable of lateral tilting movement whereby the user will be urged by the apparatus to roll over after a predetermined period of time to prevent overexposure of one surface and to permit even tanning of the user's body.

These and other objects and advantages of the invention will appear more fully from the following description made in conjunction with the accompanying drawings wherein like reference characters refer to the same or similar parts throughout the several views.

FIGURES OF THE DRAWINGS

FIG. 1 is a perspective view of the novel outdoor furniture apparatus.

FIG. 2 is an end elevational view as viewed along line 2—2 of FIG. 1 and looking in the direction of the arrows.

FIG. 3 is a vertical sectional view taken approximately along line 3—3 of FIG. 2 and looking in the direction of the arrows.

FIG. 4 is a cross-sectional view taken approximately along line 4—4 of FIG. 3 and looking in the direction of the arrows.

FIG. 5 is a cross-sectional view taken approximately along line 5—5 of FIG. 3 and looking in the direction of the arrows.

FIG. 6 is a cross-sectional view taken approximately along line 6—6 of FIG. 4 and looking in the direction of the arrows.

PREFERRED EMBODIMENT OF THE INVENTION

Referring now to the drawings, and more specifically to FIGS. 1 and 2, it will be seen that the novel article of outdoor furniture, designated generally by the numeral 10, includes a generally dome-shaped base 11 and an elongate generally horizontally oriented support 12. The article of furniture 10 is adapted to support a user in a reclining position to permit the user to sunbathe and to obtain an even tan. The dome-shaped base 11 includes a substantially flat circular bottom wall 13 which is integral with a generally dome-shaped upper member 14. The base as well as the horizontal support 12 may be formed of a suitable moldable plastic material, having the necessary strength characteristics for the intended use of the article. The dome-shaped upper member 14 has an access opening therein which is closed by an access plate secured in place on the upper member by suitable bolts. This access plate can be removed to permit access to the interior of the dome-shaped upper member 14.

Referring now to FIGS. 2 through 5, it will be seen that the dome-shaped upper member 14 is provided with an elongate generally arcuate upper reduced portion 16 which has substantially flat vertical side wall elements 17 and an arcuate upper surface 18. The arcuate upper surface 18 is provided with an elongate slot 19 therein and each vertical side wall element 17 is provided with an arcuate slot 20 therein. It is pointed out that the slots 20 in the side wall elements 17 are disposed in aligned relation with respect to each other.

The horizontal support 11 is of generally rectangular shaped configuration and includes end edges 21 and substantially elongate parallel side edges that are provided with upturned flanges 22. It will also be noted that the horizontal support 12 has a smooth concave upper surface 23 and a convex lower surface 24. The convex lower surface is provided with transverse and longitudinal ribs 25 that impart strength to the horizontal support. It will be appreciated that the ribs 25 may be formed in the horizontal support during the molding process. The upper surface of the support is provided with a suitable water impervious pad 26 which is secured to the support by any suitable securing means such as glue or the like.

The lower surface of the horizontal support 12 is provided with a downwardly facing socket 27 for accommodating the upper end of an elongate generally vertically disposed shaft 28. The shaft 28 is secured to the socket by suitable set screws 29. The shaft 28 projects through an elongate sectional shaft housing 30 including an upper section 31 and a lower section 32. The upper shaft section 31 has secured to its lower end an upper bearing housing 23, and the lower shaft section 32 has a lower bearing housing 34 secured to its upper end. These bearing housings are secured together by suitable bolts and are provided interiorly thereof with a bearing (not shown) in which the shaft 28 is journaled. The upper and lower bearing housings each have a projection 35 projecting from one side thereof and these projections are recessed, thereby defining an opening 36 for accommodating a pin or bolt 37, as best seen in FIG. 5. The end of the bolt 37 is threaded for accommodating a nut 38 which is provided with a handle 39 to facilitate turning the nut. It will be noted that the bolt 37 projects through the slots 20 and constitutes a means for releasably locking the support in a tilted or non-tilted position.

Means are provided for rotating the support and this means includes a power unit 40 positioned within the interior 11a of the dome-shaped base 11. The power unit includes an electric motor 41 provided with suitable electrical conductors 42 which are adapted to be connected to a source of electrical current. The output shaft of the electric motor is connected to a gear box 43 and the output shaft of the gear box is drivingly connected to the shaft 28. It will be seen that the gear box housing is also connected to the housing for the electric motor 41.

Referring now to FIGS. 4 and 6, it will be seen that a pivot casting 44 is positioned within the interior 11a of the dome-shaped base and is secured to the bottom wall 13 of the latter by suitable bolts. The pivot casting 44 includes a pair of upstanding plates 45, each of which is apertured at its upper end for receiving a pivot pin 46 therethrough. The pivot pins 46 project into pivot sleeves 47 which are secured to opposite sides of a bearing housing 48. Bearing housing 48 is secured to the lower end of the shaft housing 30 and is also secured to the gear box 43. Thus the pivot pins 46 actually constitute a gimbal or trundle type pivotal connection with the pivot casting 44.

It will therefore be seen that the horizontal support 12 and the entire power unit including the shaft 28 and shaft housing 30 are pivotally connected with the dome-shaped base 11 for pivotal movement about a horizontal axis to permit pivoting movement of the horizontal support 12 between tilted and non-tilted positions. The pin and slot connection between the shaft housing and the dome-shaped base permit the horizontal support to be releasably locked in a tilted or non-tilted position.

The article of furniture 10 also includes a tray 49 which is shown as positioned at approximately the same height as the horizontal support 12 by means of a vertical support post 50. The vertical support post 50 is rigidly secured to a horizontal tubular member 51 which is integral with the dome-shaped base 11. It will be seen that the electrical conductors 42 extend through the horizontal tubular member 51 and extend outwardly thereof through an opening therein.

The tray 49 has a rheostat-type switch 52 secured thereto, as best seen in FIGS. 1 and 2, and the switch is electrically connected in controlling relation with respect to the electric motor 41. The tray is adapted to support articles normally used by a sunbather, such as lotions, suntan oil and the like.

In operation, a user will lie upon the horizontal support exposing either the front or back side of the user's body to the sun. The support may be moved to a tilted position by loosening the nut 38 and adjusting the pin 37 in the slots 20. The nut may then be tightened to retain the support in the tilted position. The user will then energize the motor 41 by actuating the switch 52. When this occurs, the horizontal support will rotate in a clockwise direction at a rate of approximately two revolutions per hour. This is slightly faster than the relative rotation of the earth on its axis, but it maintains the sunbather's body in correct angular relation with respect to the sun. It will be appreciated that the user will first position the article of furniture so that the sun properly strikes the user's body at the beginning of the sunbather's sun bath.

The horizontal support will rotate while maintaining the sunbather at the proper angle to obtain optimum effect from the sun's rays. During this time, the sunbather will be lying upon the support in approximately the middle thereof or adjacent that side of the support which is disposed lowermost when the support is in the tilted condition. When the support has revolved one-half turn, the user will then be on the higher of the tilted sides and this angular tilt is sufficient to cause discomfort to the user or possibly cause the user to roll over towards the lower side by action of gravity. At that time, that portion of the user's body that is facing the sun has been exposed for approximately 15 minutes. Thus this tendency of the support to cause the user to roll towards the lower side is a means of preventing overexposure to the sun by the user.

The user will then expose the other portion of the user's body to the sun while constantly maintaining the user's body at the proper position with respect to the sun. This movement of the horizontal support as well as the tilting feature permits a user to obtain even tanning while minimizing the chance of overexposure of any particular surface area of the user's body.

From the foregoing, it will be seen that I have provided a novel article of outdoor furniture, which is of simple and inexpensive construction, and which is operable to permit a user to obtain an even suntan while minimizing the likelihood of overexposure.

While the preferred embodiments of the present invention have been described, it should be understood that various changes, adaptions and modifications may be made therein without departing from the spirit of the invention and the scope of the appended claims.

What is claimed is:

1. An article of furniture for supporting a user in a reclining position during sunning and being operable to permit the user to obtain an even suntan, comprising:
   a base structure for engaging the ground surface;
   an elongate, generally horizontal support adapted to support a user thereon in a reclining position during sunning, said support having an upper surface, a lower surface, end edges and longitudinal side edges;
   pivot means interconnecting the support with said base to permit limited lateral tilting movement of said support about an axis extending longitudinally of the latter, means interconnecting the support with said base to permit longitudinal tilting movement of said support about an axis extending transversely of the latter, and means interconnecting said support with said base permitting rotation of the support relative to the base;
   power means drivingly connected with the support for rotating the latter approximately two revolutions per hour whereby a user lying on said support will obtain an even tan on that surface of the user's body exposed to the sun.

2. The invention as defined in claim 1 wherein said support has a concave upper surface extending downwardly from the longitudinal side edges thereof.

3. The invention as defined in claim 1 wherein said base is of generally dome-shaped configuration.

4. An article of furniture for supporting a user in a reclining position during sunning and being operable to permit the user to obtain an even suntan, comprising:
   a base structure for engaging the ground surface;
   an elongate, generally horizontal support adapted to support a user thereon in a reclining position during sunning, said support having an upper surface, a lower surface, end edges and longitudinal side edges;

pivot means pivotally connecting said support with said base to permit limited lateral tilting of the support from a non-tilted position to a tilted position, said support, when in a tilted position, having one longitudinal side edge thereof disposed at an elevation higher than the other longitudinal side edge thereof, means for retaining said support in a tilted or non-tilted position, said support, when in the tilted position, tending to cause a user lying on the support to roll over by action of gravity when the support has been revolved approximately one-half rotation to thereby expose another surface of the user's body to the sun, power means drivingly connected with the support for rotating the latter approximately two revolutions per hour whereby a user lying on said support will obtain an even tan on that surface of the user's body exposed to the sun.

5. The invention as defined in claim 4 wherein said pivotal connection interconnecting the support with said base permits pivoting of the power means with said horizontal support.

6. The invention as defined in claim 4 and an elongate, generally vertically oriented shaft extending upwardly through the base and having its upper end thereof connected with said support and having its lower end connected with said power means, and a pivotal connection interconnecting said power unit and shaft with said base to permit pivoting of the power unit, shaft and support as a unit about a substantially horizontal axis.

* * * * *